US005645564A

United States Patent [19]
Northrup et al.

[11] Patent Number: 5,645,564
[45] Date of Patent: Jul. 8, 1997

[54] MICROFABRICATED THERAPEUTIC ACTUATOR MECHANISMS

[75] Inventors: Milton A. Northrup, Berkeley; Dino R. Ciarlo, Livermore; Abraham P. Lee, Walnut Creek; Peter A. Krulevitch, Los Altos, all of Calif.

[73] Assignee: Regents of the University of California, Oakland, Calif.

[21] Appl. No.: 446,146

[22] Filed: May 22, 1995

[51] Int. Cl.⁶ .................................................. A61B 17/28
[52] U.S. Cl. ........................ 606/205; 606/206; 606/207; 128/751
[58] Field of Search .................................. 606/205, 206, 606/207, 151, 211, 210; 128/751; 294/99.2

[56] References Cited

U.S. PATENT DOCUMENTS

| | | | |
|---|---|---|---|
| 4,666,198 | 5/1987 | Heiserman | 294/86.4 |
| 4,976,718 | 12/1990 | Daniell | 606/210 |
| 5,002,323 | 3/1991 | Idsund | 606/210 |
| 5,046,773 | 9/1991 | Modesitt | 294/100 |
| 5,254,130 | 10/1993 | Poncet et al. | 606/207 |
| 5,458,387 | 10/1995 | Conway et al. | 294/100 |

*Primary Examiner*—Michael Powell Buiz
*Assistant Examiner*—Mark S. Leonardo
*Attorney, Agent, or Firm*—Henry P. Sartorio; L. E. Carnahan

[57] ABSTRACT

Electromechanical microstructures (microgrippers), either integrated circuit (IC) silicon-based or precision machined, to extend and improve the application of catheter-based interventional therapies for the repair of aneurysms in the brain or other interventional clinical therapies. These micromechanisms can be specifically applied to release platinum coils or other materials into bulging portions of the blood vessels also known as aneurysms. The "micro" size of the release mechanism is necessary since the brain vessels are the smallest in the body. Through a catheter more than one meter long, the micromechanism located at one end of the catheter can be manipulated from the other end thereof. The microgripper (micromechanism) of the invention will also find applications in non-medical areas where a remotely actuated microgripper or similar actuator would be useful or where micro-assembling is needed.

30 Claims, 10 Drawing Sheets

MICROFABRICATED THERAPEUTIC ACTUATOR MECHANISMS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microstructures, particularly to electromechanical micromechanisms, and more particularly to microgrippers for use in catheter-based interventional therapies or remote micro-assembly applications.

Microactuators for remote and precise manipulation of small objects is of great interest in a wide variety of applications. The design and development effort of such microgripper devices would be useful in the art as such will apply to general microfabrication techniques and establish the infrastructure for microengineering efforts including robotics, microtechnology, prevision engineering, defense, energy, and biomedical research, as well as use in medical applications, such as for catheter-based interventional therapies and remote assembly or use of micromechanical system.

When a portion of a blood vessel weakens, it bulges and forms a aneurysm, which is one of the main reasons for strokes as the vessel finally collapses and opens. These aneurysms have traditionally been treated by surgery, where the surgeon will have to open up the area of repair before attempting to surgically repair the aneurysm by clipping it. However, many aneurysms are at critical locations such as in the brain and are either difficult and risky to operate on or it is simply impossible. For the last 20 years, pioneering doctors have used interventional neuroradiology techniques to aid the treatment of brain aneurysms. Long (1–2 meters) and narrow (i.e. 250 μm to 500 μm) catheters are pushed through the arteries in the groin up to the brain to reach the aneurysm. Existing catheter-based interventional instruments rely on simplistic and usually singular means of actuation. These techniques, including balloon angioplasty, are well-established for large vessel treatments such as in the heart. It is crucial that in order to extend this medical practice into the smaller vessels such as those in the brain, the catheter-based tools must be miniaturized. In the most recent method, platinum coils were selected to fill up the aneurysms due to its ability to fill up irregular shapes and its resistance to electrolysis in the vessels when it is charged. The coils are either pushed through the catheter to the aneurysm by a guide wire or released by the electrolytic dissolution of a solder joint between the guide wire of the catheter and the therapeutic device, which for neurological treatments are approximately 250 μm or less in diameter. Although the charging of the coil causes electrothrombosis around the coil, the time required to release the coil is long (4 mins to 1 hr) and many coils are usually needed to fill up a regular size aneurysm. The extent to which the dissolved material affects the body is unknown and electrolysis soldering requires long terms of current in the brain and sometimes is simply unreliable. These difficulties present potential life-threatening problems to the patient for the surgeon and clinician.

Thus, there is a need for a micromechanism which can fit into a 250 μm diameter area and which would enable the physician to release and retrieve the coils or other therapy once it is released at the wrong time or location. The present invention satisfies this need by providing a micromechanical release mechanism by which this procedure becomes a safer and more reliable alternative to surgery, and which can fit into blood vessels of the brain, a 250 μm diameter area. The electromechanical microstructures, including microgrippers, can be fabricated using known IC silicon-based techniques or precision micromachining, or a combination of these techniques. While the invention has application in various areas requiring a remotely actuated microgripper, it has particular application in catheter-based interventional therapies.

SUMMARY OF THE INVENTION

It is an object of the invention to provide an electromechanical microgripper.

A further object of the invention is to provide a microgripper with a large gripping force, a relatively rigid structural body, and flexibility in function design.

A further object of the invention is to provide an electromechanical micromechanism mounted at one end of a catheter and which can be manipulated from the other end, thereby extending and improving the application of catheter-based interventional therapies.

Another object of the invention is to provide a microgripper capable of operating in an area as small as a 250 μm diameter, such as in the blood vessels of the brain.

Another object of the invention is to provide a microgripper which can be used to integrate heaters and strain sensors for remote active heating and feedback control.

Another object of the invention is to provide a microgripper which can be used as a biopsy tissue sampler, or for use as a tip designed for handling microparts.

Another object of the invention is to provide a microgripper which has the potential to apply alternative actuation mechanisms, either hydraulic or simply thermal bimorphic.

Another object of the invention is to provide a microgripper with a large gripping force (40 mN), wherein actuation thereof is generated by shape-memory alloy thin films and the stress induced can deflect each side of a microgripper up to about 55 μm for a total gripping motion of about 110 μm.

Other objects and advantages of the present invention will become apparent from the following description and accompanying drawings. Basically, the invention involves an electromechanical micromechanism which can be utilized in medical as well as non-medical applications, and is particularly applicable for catheter-based interventional therapies for the repair of aneurysms in the brain, or other small blood vessels. The microgripper of this invention has: 1) a large gripping force, 2) a relatively rigid structural body, 3) can be utilized in a 250 μm diameter area, 4) allows for flexibility in shaping the gripping jaws, 5) can be used for biopsy sampling or for handling microparts, 6) has fast release and retrieve capabilities, 7) can be integrated with heaters and strain sensor for remote active heating and feedback control, 8) may be used with hydraulic or simple thermal bimorphic actuation, and 9) may be constructed using conventional integrated circuit silicon-based techniques or precision micromaching, or both.

BRIEF DESCRIPTION OF THE DRAWINGS

The accompanying drawings, which are incorporated into and form a part of the disclosure, illustrate embodiments of the invention and, together with the description, serve to explain the principles of the invention.

FIGS. 10, 10A and 10B illustrate an embodiment of the heater of FIG. 8A, with cross-sections as shown in FIG. 10A and 10B greatly enlarged.

DETAILED DESCRIPTION OF THE INVENTION

The invention is an electromechanical grip/release micromechanism referred to thereinafter as a microgripper or microclamper. The microgripper has a large gripping force, a relatively rigid structural body, and flexibility in functional design such that it can be used, for example, as a biopsy tissue sampler, a tip designed for handling microparts, or as a release/retrieval mechanism for items such as platinum coils or other materials in bulging portions of the blood vessels, known as aneurysms. The microgripper of this invention is particularly useful to extend and improve the application of catheter-based interventional therapies, and is capable of use in a 250 μm diameter area, such as a small blood vessel of the brain. The microgripper may be constructed with outer surfaces which can be used to integrate heaters or strain sensors for remote active heating and feedback control. One embodiment of the microgripper, for example, is of a silicon structure and incorporates shape-member alloy (SMA) thin films, and the stress induced can deflect the sides thereof to enable a gripping motion of about 110 μm. The microgripper can be fabricated by precision micromachining or by techniques utilized in the fabrication of silicon-based integrated circuits.

The ultimum objective of the grip/release mechanism or microgripper is to achieve the following: 1) the cross-section should fit into a diameter as small as a 250 μm area (open and closed); 2) the release of materials into the blood vessels should be less than 10 seconds; 3) the temperature range should be between 0° C. and 37° C.; 4) current should be less that 10 mA, for example, if electrical energy is used; 5) 100% reliability.

Figure 1A:
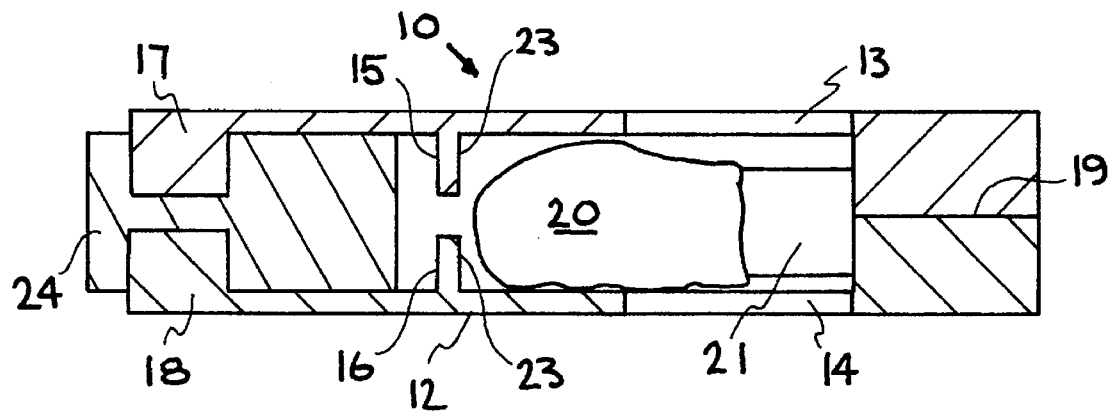
FIGS. 1A and 1B are cross-sectional views of an embodiment of the microgripper using balloon activation, and shown in the closed and open positions.
Figure 1B:
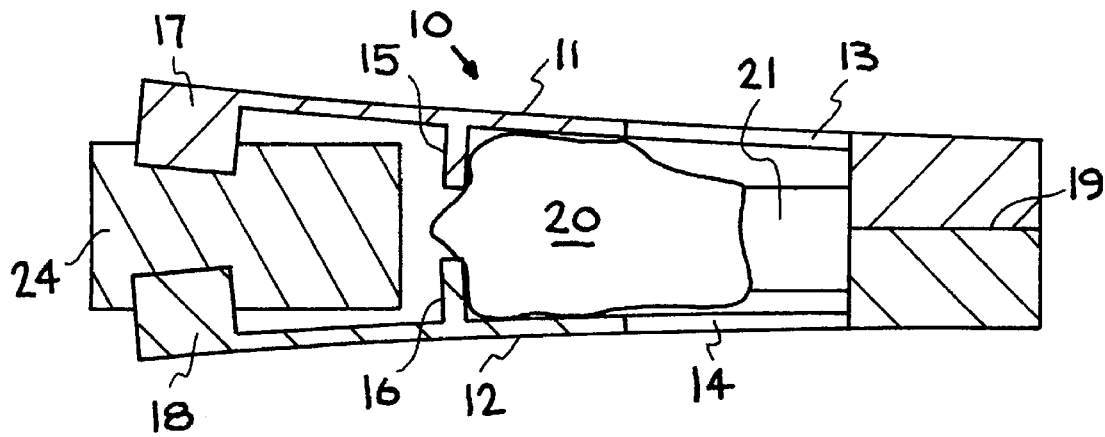
Figure 2:
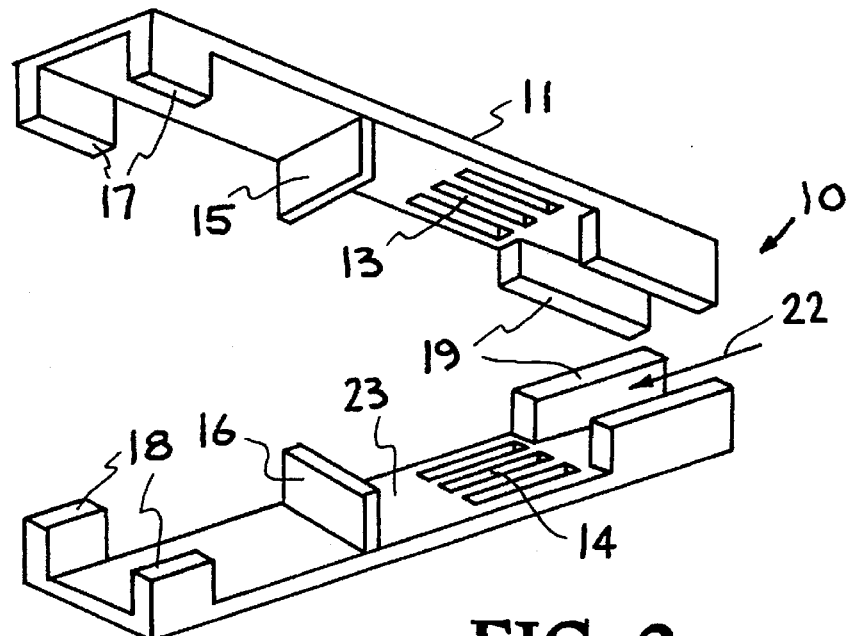
FIG. 2 is an exploded view of the FIGS. 1A–1B embodiment, with the balloon omitted.

Using conventional silicon bulk micromachining techniques a mechanical clamper or microgripper as illustrated in FIGS. 1A, 1B, and 2 can be fabricated to include a cantilever structure therein which, for example, is about 800 μm in length and the total height of the structure is 250 μm. Then a silicon microballoon may be utilized to mechanically deflect the cantilever arms to clamp onto foreign objects at the front end thereof, as seen in FIG. 1A and 1B. The microballoons are well characterized and can withstand pressures of up to 10 atm. Such microballoons have also been tested for use in human blood vessels. As seen in FIGS. 1A–1B and FIG. 2, the balloon activated microgripper generally indicated at 10 comprises a pair of jaws, grip arms, or gripping members 11 and 12, each having a plurality of slotted cantilevers 13 and 14, a pusher pad 15 and 16, and grippers 17 and 18. For some applications the pusher pads may be omitted. The jaws or gripping members 11 and 12 are bonded or otherwise secured together as indicated at 19. An expandable device, such as a balloon 20, is positioned between gripping members 11 and 12 and connected to a delivery tube or catheter 21 which extends along the balloon path 22 (See FIG. 2) through which an activating fluid or gas is supplied to activate (expand) the balloon 20. Pusher pads 15 and 16 serve as balloon force points 23 (See FIG. 2), and when fully expanded an end of the balloon may extend between the pusher pads 15–16 as shown in FIG. 1A.

With the balloon 20 in inactivated (unexpanded) position as shown in FIG. 1A, the grippers 15 and 16. Upon activation enlargement of the balloon 20, the outer ends of gripping members 11 and 12 bend or flex outwardly at the location of slotted cantilevers 13 and 14 causing the grippers 17 and 18 to separate, allowing the material 24 retained therebetween to be removed therefrom, as shown in FIG. 1B.

The gripper members 11 and 12 may be constructed of silicon, aluminum, nickel or other compatible metals, teflon or other compatible polymers, and ceramics with a length of 0.8 mm to 1.5 mm, and a width and combined height preferably not greater than about 250 μm. The balloon 20 may be a silicone microballoon capable of withstanding pressures of up to 10 atmospheres, supplied through the tube 21, which may be constructed of teflon or other inert plastics having a diameter of 80 μm to 400 μm The balloon 20 may be replaced with other expandable devices. The bond 19 may be formed, for example, by selective eutectic bonding. The pusher pads 15 and 16 have, for example, a thickness of 20 μm to 40 μm, and grippers 17 and 18 may have a thickness of 90 μm to 150 μm and length of 50 μm to 150 μm. The slotted cantilevers 13 and 14 may be composed of 3 to 10 slots having a width of 5 μm to 100 μm and length of 50 μm to 500 μm. The slots of the cantilevers may be straight or tapered along the length thereof. The material that the gripper members 11 and 12 is constructed from must be inert to the fluid or chemicals involved.

Figure 3A:
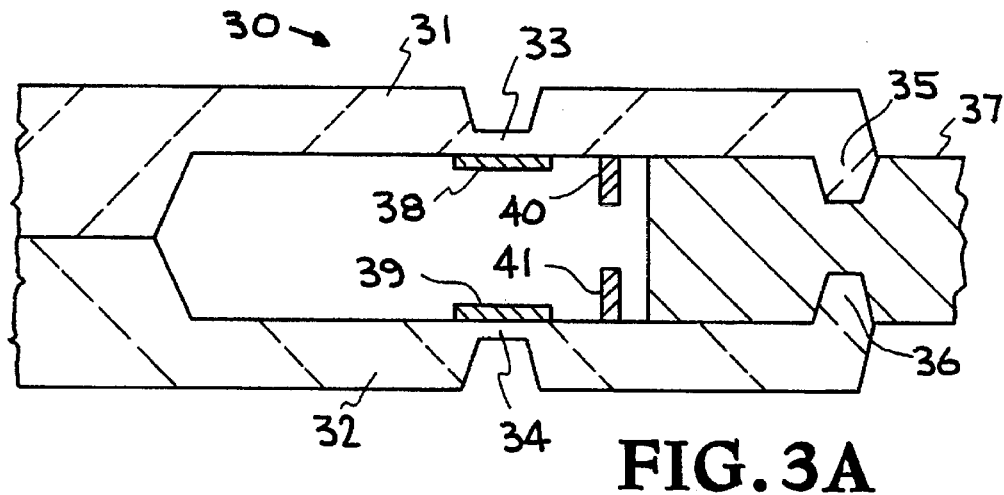
FIGS. 3A and 3B illustrate another embodiment of the microgripper using a thin film tweezer-like activator.
Figure 3B:
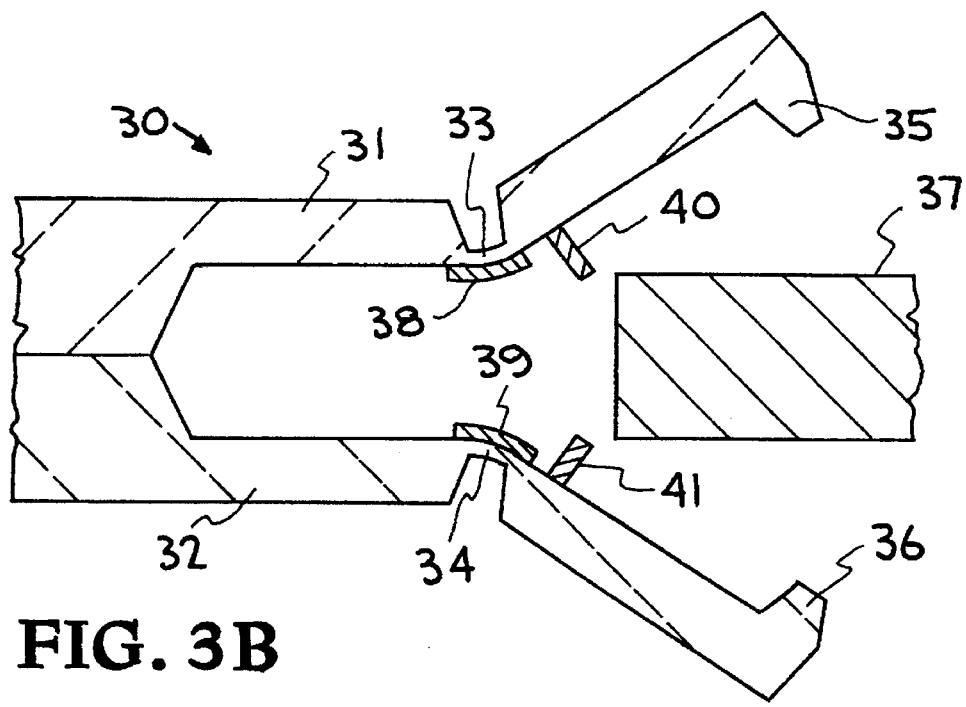

The embodiment of FIGS. 3A and 3B utilizes a pair of initial SMA thin film hinges to open and close the grip arms or gripping members according to the temperature the SMA thin film is exposed to. The SMA thin films of FIGS. 3A and 3B can also be replaced by a heater sandwiched by polyimide layer expands and deflects the cantilever clampers or grippers.

As shown in FIGS. 3A and 3B, the microgripper, generally indicated at 30 is composed of a pair of grip arms or gripping members 31 and 32 formed, for example, from silicon wafers, and each included a reduced thickness of cross-section area 33 and 34 and a pair of inwardly directed spaced grippers 35 and 36 only one gripper of each pair being shown, which retain a material or part 37, such as a stem of a platinum cell (See FIG. 3A). Thin films 38 and 39 are secured to gripping members 31 and 32 adjacent the reduced areas 33 and 34, with films 38 and 39 being constructed of SMA or polyimide layers as described above. The gripping members 31 and 32 are also provided with pusher pads 40 and 41. Upon heating of the thin films 38 and 39 by a heater, not shown, the films expand causing outward flexing or bending of the outer ends of gripping members 31 and 32 at areas 33 and 34 causing the grippers 35 and 36 to separate (See FIG. 3B) whereby material 37 is removed therefrom.

By way of example, the grip arms or gripping members 31 and 32 may be constructed of silicon, or compatible metals, polymers, or ceramics with an overall combined height and width thereof preferably not to exceed 250 µm, with the thickness of members 31 and 32 being 20 to 100 µm, with reduced areas 33 and 34 having a thickness of 5 to 15 µm, and grippers 35 and 36 extending inwardly from members 31 and 32 a distance of 20 to 50 µm. The pusher pads 40 and 41 may for example, having a thickness of 20 to 40 µm and depth (height) of 30 to 100 m. The thin films 38 and 39, if constructed of SMA, may be composed of Ni—Ti, Ni—Ti—Cu, or other low temperature SMA, having a thickness of 2 to 5 µm, and if composed of polyimide, for example, having two layers of a thickness of 3 to 10 µm and length of 300 µm to 500 µm, which sandwich therebetween a heater constructed of Ti—Au. Heating of the SMA films 38 and 39 is accomplished, for example, by integrating polysilicon heaters or direct resistive heaters of SMA, as described hereinafter with respect to FIGS. 9 and 10, or by laser heating through optical fibers. Shape-memory alloys are well known, as evidenced by U.S. Pat. No. 5,061,914 issued Oct. 29, 1991 to J. D. Busch et al.

The embodiment of FIGS. 1A-1B and 3A-3B can also be utilized to retrieve material or parts, such as platinum coils used to repair aneurysms. These embodiment have advantages over prior known microgrippers that are electrically conductive (see C. J. Kim et al, "Silicon-Processed Overhanging Microgripper", Journal of Microelectromechanical Systems, Vol. 1, No. 1, pp. 31-36, March 1992) and can be used to manipulate biological cells or micro parts for assembly.

Figure 4A:
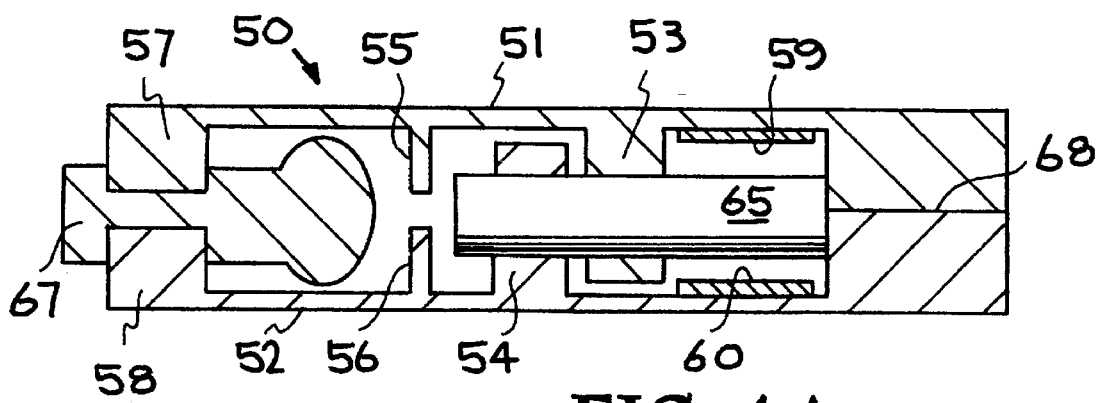
FIGS. 4A and 4B are cross-sectional views which illustrate another embodiment of the microgripper using a shape-memory alloy (SMA) wire clicker.
Figure 4B:
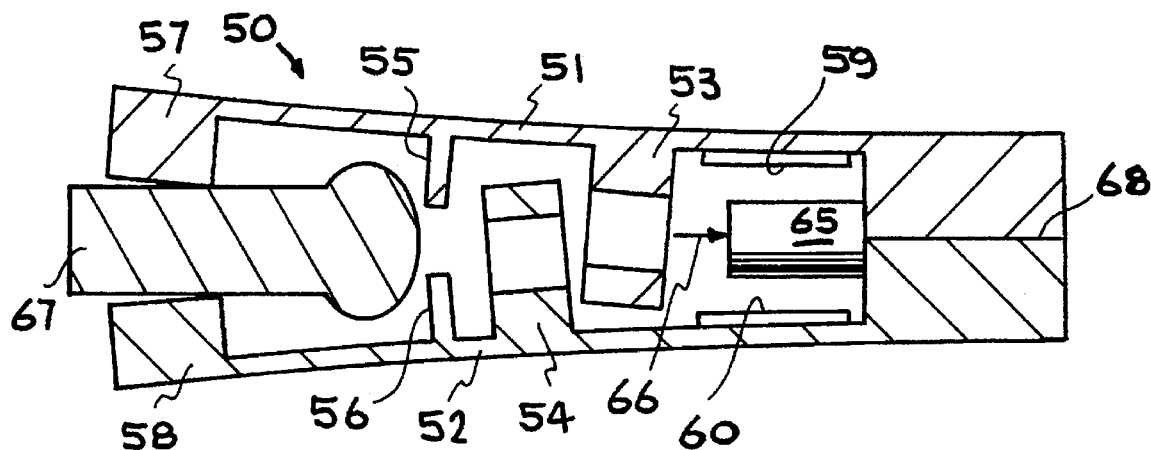
Figure 5:
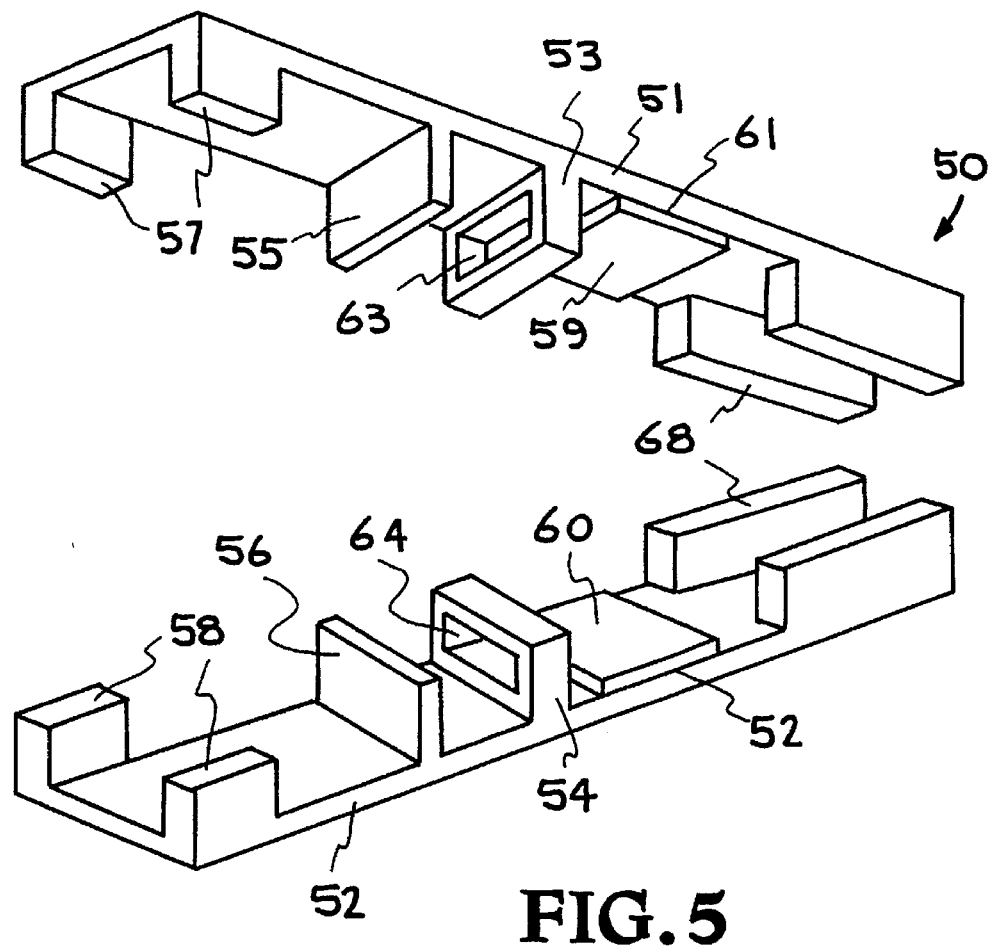
FIG. 5 is an exploded view of the FIGS. 4A–4B embodiment with the SMA wire omitted.

The embodiment of FIGS. 4A-4B and FIG. 5 is a microgripper that is a normally open release mechanism (FIG. 4B), where an SMA wire is used as a latch to close the microgripper (FIG. 4A), and when activated to click open the mechanism. As shown, this embodiment, generally indicated at 50, comprises a pair of grip arms or gripping members 51 and 52, generally similar in construction to the gripping members 11 and 12 of the FIGS. 1A-1B embodiment, and are provided with hook connectors 53 and 54, pusher pads 55 and 56, and pairs of grippers 57 and 58, only one each shown. A compressive thin film 59 and 60 is secured in openings 61 and 62 of gripping members 51 and 52. Hook connectors 53 and 54 have opening 63 and 64 (see FIG. 5) through which an SMA wire 65 extends (see FIG. 4A) to "close" the gripping members 51 and 52 and compress the compressive thin films 59 and 60. Upon activation of the SMA wire 65, the wire is withdrawn from openings 63 and 64 of hook connector s 53 and 54, as indicated by the arrows 66 (see FIG. 4B), whereupon the compressive thin films 59 and 60 expand causing the ends of gripping members 51 and 52 to flex or bend outwardly. In the closed position (see FIG. 4A) the pairs of grippers 57 and 58 retain a material or part 67 therebetween, and upon activation or clicking open of the latch (hook connectors 53 and 54 and SMA wire 65), the grippers 57 and 58 move outwardly allowing the material or part 67 to be removed from therebetween. As in the embodiment of FIGS. 1A-1B, the gripping members 51 and 52 are bonded together as indicated at 68.

By way of example, the gripping members 51 and 52, pusher pads 55 and 56, and grippers 57 and 58 may be constructed and configured as described above in the FIGS. 1A-1B embodiment. The hook connects 53 and 54 are composed of silicon, metals, polymers or ceramics and secured, as by micromachining, and having a height of 80 to 200 µm, width of 200 to 500 µm and the openings 63 and 64 therein have a cross-section of 80 to 380 µm, width of 180 to 480 µm, and may be configured other than square. The SMA wire 65 may be composed of Ni—Ti—Cu, Ni—Ti, or Ni—Ti—Hf, having a cross-section and configuration which corresponds with the openings 63 and 64 of hook members 53 and 54. The compressive thin film 59 and 60 may be constructed of silicon dioxide, doped polysilicon, or polymers having a thickness of 3 to 8 µm, and cross-section of 250×250 or 250×400 µm.

Figure 6:
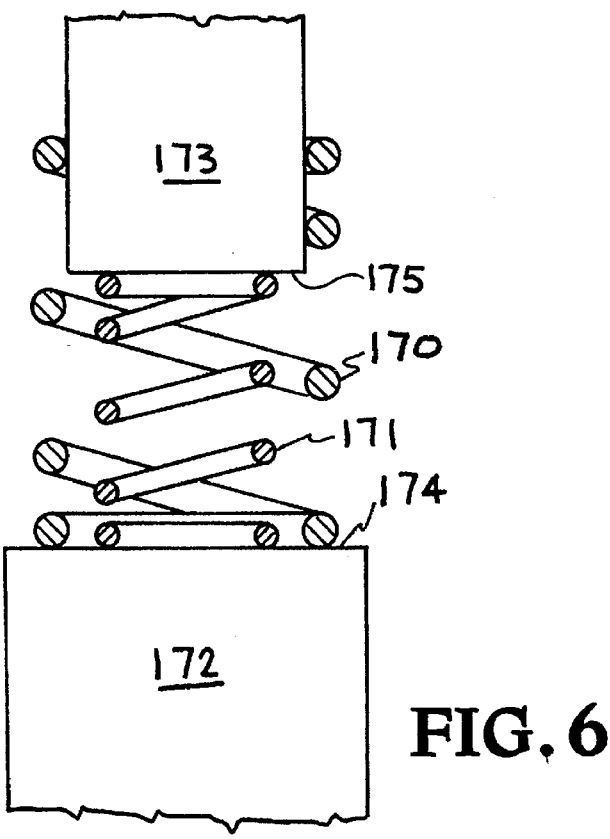
FIG. 6 is an embodiment of the invention using SMA double coils.

FIG. 6 illustrates a microgripper using two SMA microcoils, one to grip on to the stem of a platinum coil, for example, and the other one to push the platinum coil outwards to assure the release, the micro-coils being secured at one end to the tip of a guide wire, such as used in catheter-based interventional therapies. As shown in FIG. 6, two SMA coils 170 and 171 are secured at one end to a guide wire 172. Coil 170, of substantially greater cross-section and of greater diameter than coil 171, extends (wraps around coil 171 and around an end of a stem 173 of a platinum cell, for example, and retains or grips the stem 173. The coil 171 extends between the tip 174 of guide wire 172 and end 175 of stem 173. Under normal conditions the coil 170 retains the stem 173 from moving, and upon activation the coil 171 expands pushing the stem 173 out of the coil 170.

By way of example, the larger coil 170 may be constructed of SMA wire having a diameter of 50 to 75 µm, a number of turns or wraps ranging from 10 to 15, and constructed of Ni—Ti, Ni—Ti—Cu, or Ni—Ti—Hf. The smaller coil 171 may be constructed of SMA wire composed of Ni—Ti, Ni—Ti—Cu, and Ni—Ti—Hf, having a diameter of 30 to 50 µm, with the turns or wraps ranging from 5 to 10. The micro-coils 170 and 171 may be secured to guide wire 172 by bonding, soldering, etc.

Figure 7:
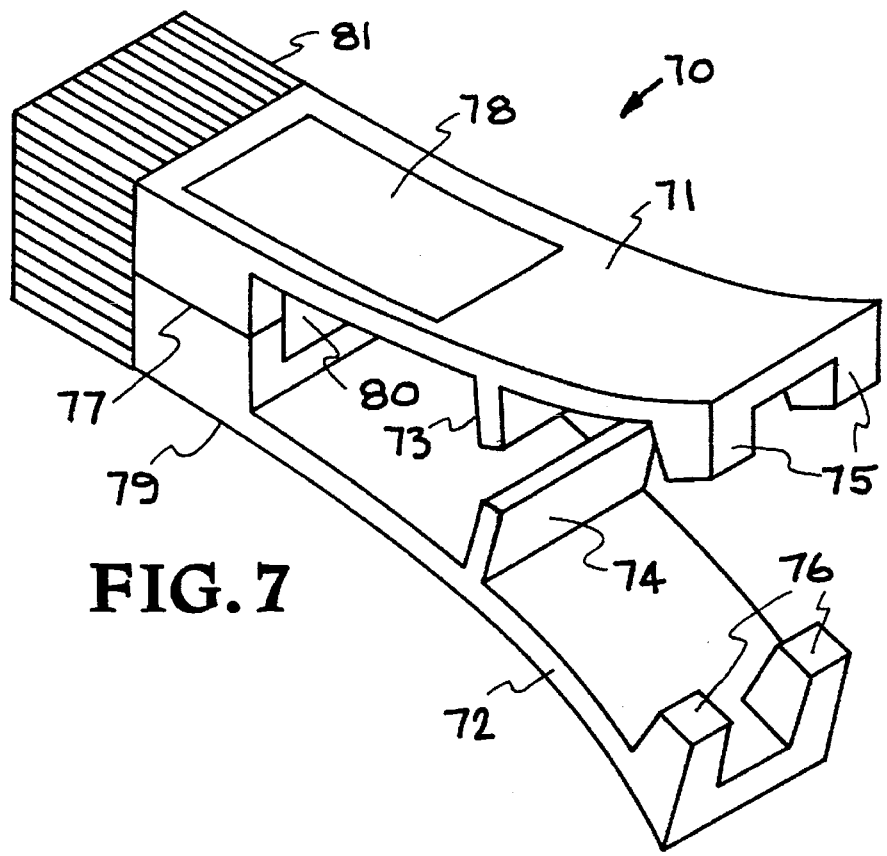
FIG. 7 is a preferred embodiment of a silicon microgripper made in accordance with the present invention.

The preferred embodiment of FIG. 7 uses a combination of silicon structure and SMA thin film, and is provided with a wiring jacket for signal input. This embodiment provides a microgripper that can be locally actuated at low temperatures (<100°C.), with a large gripping force (10 to 40 mN), a relatively rigid structural body, and flexibility in functional design. Also, this microgripper has the capability to lock the target gripping object. The actuation of the microgripper is generated, for example, by NiTiCu shape-memory alloy thin films and the stress induced can deflect each side of the microgripper up to 55 µm for a total gripping motion of 110 µm. This opening motion corresponds to a 20 mN opening force on the tip of the gripper. In addition the microgripper can work in a liquid environment. The opening jaws, the pusher pads, and the hollow channel are shaped by a combination of precision sawing and bulk machining of silicon. Two preprocessed silicon wafers are prevision aligned and selectively bonded, using an Au—Si eutectic process which involves aligning a mask on a wafer and evaporating through the mask onto the gripper bonding portion, as described in greater detail hereinafter with respect to FIG. 8. The microgripper of FIG. 7 is 1 mm×200 µm×380 µm in dimension, having a pair of silicon cantilevers 12.5 µm thick, with 5 µm thick NiTiCu SMA thin films deposited on the outer sides of the cantilevers or gripper arms to provide actuation of the microgripper. The SMA thin film can generate actuation stresses up to 500 MPa at transformation temperatures between 30° C. to 70° C., which is a lower temperature than all known thermal bimorphic microgrippers. For experimental verification, the microgripper was actuated by external heating and a video tape was prepared to demonstrate the opening and closing motions.

Referring now to a specific embodiment as shown in FIG. 7, the microgripper generally indicated at 70 includes a pair of silicon cantilevers, gripper arms or gripping members 71 and 72, each member 71 and 72 having a 30 µm wide pusher pad indicated at 73 and 74, respectively, and a pair of 60×110×100 µm³ gripping jaws or grippers 75 and 76. The gripping members 71 and 72 are Au—Si eutectic bonded together at an interface 77, and are each provided with an SMA thin film 78 and 79 on the outer surfaces or sides thereof. The cantilevers or gripping members 71 and 72 are constructed to define a 110 µm wide hollow channel 80 in the area of the bonded interface 77, which is in communication with one end of a catheter, for example, on which the microgripper is mounted. The microgripper 70 is secured to a wiring jacket, generally indicated at 81, for signal inputs.

The composition of the gripping members 71 and 72, the SMA thin films 78 and 79, the eulectic bond 77, and the dimensions of the microgripper 70 have been set forth above. By way of example, the pusher pads 73 and 74 may have a thickness of 20 to 40 µm and height of 80 to 100 µm; with the gripper 75 and 76 having a height of 80 to 100 µm, and end cross-section of 70×150 µm; and with the hollow channel 80 having a width of 100 to 250 µm and height of 50 to 180 m.

The fabrication of the microgripper embodiments of FIGS. 1A–1B, 3A–3B, 4A–4B, and 7, particularly FIG. 7, allows the designer some flexibility in shaping the gripping jaws as the targeting specimens dictate, and can either be used as a biopsy tissue sampler or a catheter tip designed for handling microparts. The outer surfaces of the microgripper, particularly FIG. 7, can be used to integrate heaters or strain sensors for remote active heating and possible feedback control as described hereinafter with respect to FIGS. 9–12. The hollow channel of the FIG. 7 embodiment has the potential for either wire connection or injection of liquids and therapeutic medicine. Another important advantage is the possibility to apply alternative actuation mechanisms on the microgripper structure, either hydraulic or simply thermal bimorphic. Many creative designs of practical microgrippers for various applications can be conceived using this basic approach. Fabrication process steps can be highly automated and batch fabrication of the microgrippers will reduce the manufacturing cost.

Applications of the FIG. 7 microgripper include assembling small parts for manufacturing, minimally-invasive in vivo biopsy tissue sampling, catheter-based endovascular therapeutic procedures, and remote handling of small particles in extreme environments (high/low pressures, hazardous fluids, etc.).

The microfabrication process for the FIG. 7 embodiment can be categorized into bulk micromachining, fine alignment, etching, and Ni—Ti—Cu SMA thin film deposition. As set forth above, a specific embodiment of the FIG. 7 type microgripper is 1000×200×380 µm³ in dimension. Each silicon cantilever (72 and 73) is 125 µm thick and 5 µm En Ni—Ti—Cu SMA thin films (78 and 79) are deposited on the outer surfaces of the cantilevers for actuation thereof. The pusher pads (73–74) are 30 µm wide while the gripping jaws (75–76) are 60×110×100 µm³. The hollow channel 80 is 110 µm wide and 175 µm in height. The gripping jaws, pusher pads, and hollow channel are shaped by a combination of precision sawing and bulk machining of silicon, and thus can be batch fabricated. The connection of the microgripper to external leads and milli-end effectors (as exemplified in FIG. 9) requires assembly and therefore does not allow for batch fabrication. However, there is an ongoing effort to develop assembly techniques for packaging.

The cantilevers or gripper arms (71–2) of the microgripper are fabricated on two silicon wafers. This process starts with two 100 µm thick (110) p-type silicon wafers, which are ground and polished from a width of 200 m to an overall width of 380 m. The common masking film for patterning and etch silicon was 1000 Å of silicon nitride.

A test pattern is essential to identify the exact (111) plane as opposed to the wafer flat, which is typically offset 2°–3°. Alignment targets are imprinted on each of the silicon wafers using this crystal plane identifying pattern to ensure the subsequent aligning to the exact crystal planes. Two types of alignment targets must be defined, one to carry out front-to-back alignment and another etched through the wafers to provide holes for precise pin mechanical alignments for eutectic bonding. Dicing line (2 µm deep) are then patterned on the backside of each wafer. On the front side of each wafer, saw cut channel guide lines are patterned for the precision saw to form the silicon cantilevers (7–72) and the pusher pads (73–74). These patterns are imprinted by etching the silicon down 1 µm. After reapplying the masking silicon nitride, lathography is carried out for the gripping jaws (75–76) and the hollow channel (80). The silicon wafers are then etched in 44% KOH, creating vertical walls 85 µm deep. The silicon nitride mask is then stripped and ready for the precision saw, such as a model 780 by Kulicke & Sofia, with positioning accuracies as high as 2.5 µm. Precision sawing was chosen to avoid the anisotropic etching limitations of silicon that does not allow vertical wall etch channels 90° apart without careful corner compensation and sacrifice of finished surfaces. Since the width of the two cut channels are 200 µm and 400 µm, respectively, the blade selected was 200 µm thick. The wider cut channel (400 µm) was formed by making two adjacent saw cuts. The saw was indexed to leave a pusher pad (73–74) width of 30 µm. For careful control of the cut depths, it is necessary to index the depth from the bottom of the wafer. Furthermore, it is ideal to dress the blades on rougher surfaces to achieve the vertical edges. The pair of silicon cantilevers or gripper arms (71–72) formed from the silicon wafers are now reading for bonding.

Bonding of the cantilever or gripper arms of FIG. 7, for example, is carried out using Au—Si eutectic bonding, whereby selective areas of bonding at a low temperature (<400° C.) is achieved. The silicon microstructures, such as the gripper arms of FIG. 7 can be bulk micromachined on two silicon wafers, as described above, and then eutectic bonded, which enables designer to designer minimal gap microstructures that can also be applied as capacitance sensors/actuators and microfluidics systems with fight seals.

Figure 8:
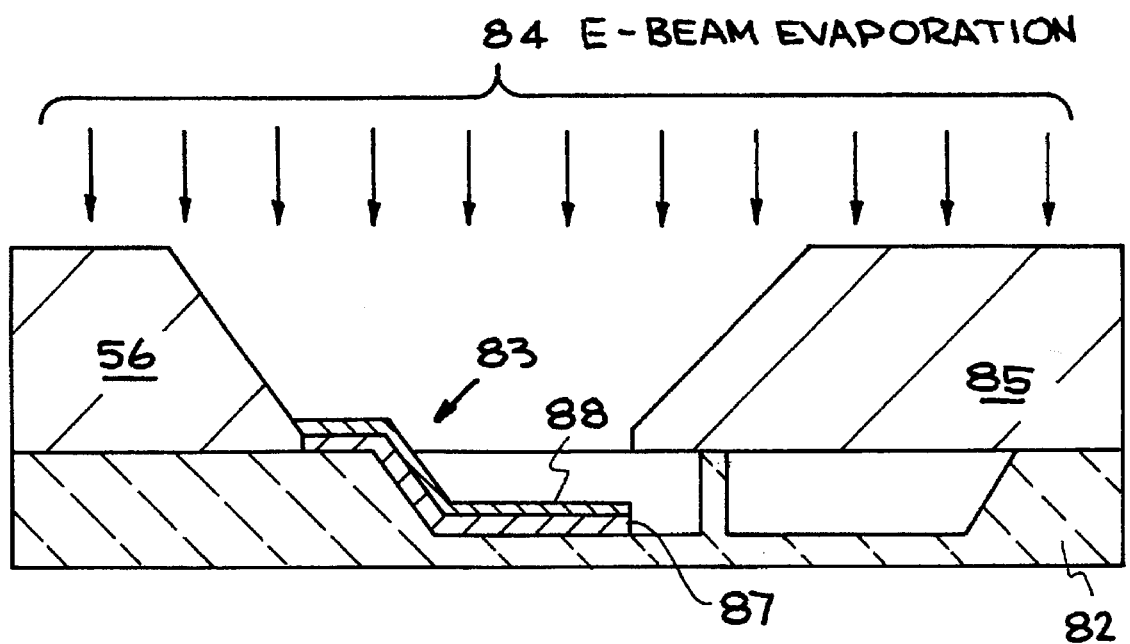
FIG. 8 is a cross-sectional view illustrating the eutectic bonding process.

Using Au—Si eutectic bonding a microstructure, composed of the two silicon machined wafers, such as illustrated in FIG. 7 may be fabricated as illustrated in FIG. 8. On each cantilever 82 framed from a silicon wafer, Ti/Au pads, generally indicated at 83, 500×500 m in area for example, are deposited by electron beam (E-Beam) evaporation indicated at 84, by arrows and patterned through shadow masks 85 and 86, such as illustrated in FIG. 8. The Ti layer 87 is an adhesive layer and also serves as a diffusion barrier for Au layer 88. The thickness of the pads 83 are, for example, 500 Å for Ti (layer 87) and 1 µm for Au (layer 88). The annealing temperature is 370° C. to 390° C. which is above the 363° C. eutectic point to assure the interface to liquidify. Soaking at this temperature for 5 minutes is necessary. The shadow masks 85–86 are currently fabricated by etching windows out of (100) silicon wafers. By aligning the shadow masks to the wafer only areas coated with Ti/Au will be bonded together. The mating silicon wafers should have a fully cleaned silicon surface where the bonding is to occur. The wafers are then pressurized together and held in low vacuum (nominally $10^{-4}$ Torr) and soaked, for example, at 380° C. for three (3) minutes. An acoustic image of an array of Ti/Au eutectic bonding pads 83 seen through a pair of 2 inch silicon wafers showed that a highly uniform and solid bond has been formed. The Au—Si bond strength was measured in an instron pull test, where 9 eutectic bond pads were pulled and failed at pull stress of 5.5 GPa. The eutectic bond areas were intact, as fracturing of the silicon surrounding the bond areas occurred in the process.

During the bonding process, mechanical alignment using precise diameter pins were applied to ensure controlled processing and prevent shattering of the fragile thin cantilevers. The bonded pair of cantilevers (71–72) are now ready for deposition of the SMA thin films (78–79).

The SMA thin films are composed of Ni—Ti—Cu deposited using a mixed dc magnetron sputtered deposition, the details of the mixed sputtering process are set forth in copending application Ser. No. 08/(IL-9463), filed May 1995, entitled, "Multiple Source Deposition Of Shape-Memory Alloy Thin Films" and assigned to the assignee of this application. In that sputtering process, three (3) separate targets are used to sputter the alloy such that the power can be individually controlled to actively determine the alloy composition. The thin film was deposited at 505° C., for example, so that it is in situ annealed to relieve the residual stress. The SMA film was initially deposited sequentially on the outer sides or surface of the cantilever arms (71–72) of FIG. 7, for example, so that one side is annealed twice at 505° C., but preferably deposition of the SMA film prior to bonding of the cantilever arms would reduce thermal stress in the film. The following sets forth a concise process sequence for fabricating a micro-actuator, such as illustrated in FIG. 7, the sequence includes:

a) pattern crystal plane test marks, align targets and alignment holes.

b) pattern saw cut channel guide lines.

c) pattern silicon etch channels following the (111) plane direction.

d) anisotropic etching of the silicon etch channels by KOH.

e) shadow mask alignment to wafer, and deposition of Ti/Au film.

f) mechanical pin alignment and eutectic bonding at 380° C. (3 min.) and $10^{-4}$ Torr.

g) magnetron sputter deposition of Ni—Ti—Cu films on both sides with in situ annealing at 505° C.

h) dice up individual microgrippers.

The microgripper of FIG. 7, is actuated using the dc magnetron sputtered nickel-titanium-copper-shape memory film. Shape memory actuation is based on a crystalline phase transformation in which the low temperature phase (martensite) is easily and reversibly deformable via twins, while the high temperature phase (austenite) has one rigid configuration. The $Ni_{42}Ti_{50}Cu_8$ alloy transforms just above body temperature (37° C.), making it useful for implantable medical devices, and has a narrower hysteresis than binary nickel-titanium which increases efficiency and improves response time. Furthermore, the addition of copper makes the transformation temperature less sensitive to film composition.

In the microgripper application, actuation occurs by the recovery of tensile residual stress in the memory film, the data thereof being obtained by measuring substance curvature as a function of temperature. The film, which is deposited at 500° C., develops a tensile thermal stress as it is cooled after deposition. When cooled below the temperature at which the martensitic transformation starts, the thermal stress in the film can relax by twin-related deformation. This tensile thermal stress can be recovered by heating the film. Thus, the silicon microgripper cantilevers act as bias springs which are opened by the contracting shape-memory film (78–79) when heated, then deflected back to a neutral position and stretch the shape-memory film when cooled. Films with up to 500 MPa recoverable stress have been deposited, but the film on the cantilevers of FIG. 7, for example, have a recoverable stress of 375 MPa. Testing of the stress induced by the Ni—Ti—Cu film was measured by a Tencor FLX—2320 laser system, which measures the curvature induced by the film on an Si substrate, which is translated into stress.

In order to evaluate the gripping force induced by the Ni—Ti—Cu SMA film, an equivalent model with an opening force at the tip was assumed. By applying bimetallic stress equations, the relation between the Ni—Ti—Cu film stress and the deflection of the gripper tip was calculated. For a film thickness of 5 µm, the deflection is calculated to be 53 µm. Experimental results showed the gripper opening to 55 µm when fully actuated. Using the equivalent model, it was found that it requires 20 mN to deflect the microgripper to 55 µm. Therefore, a gripping force of 40 mN (20 mN on each cantilever) is applied for a fully open microgripper.

Figure 10:
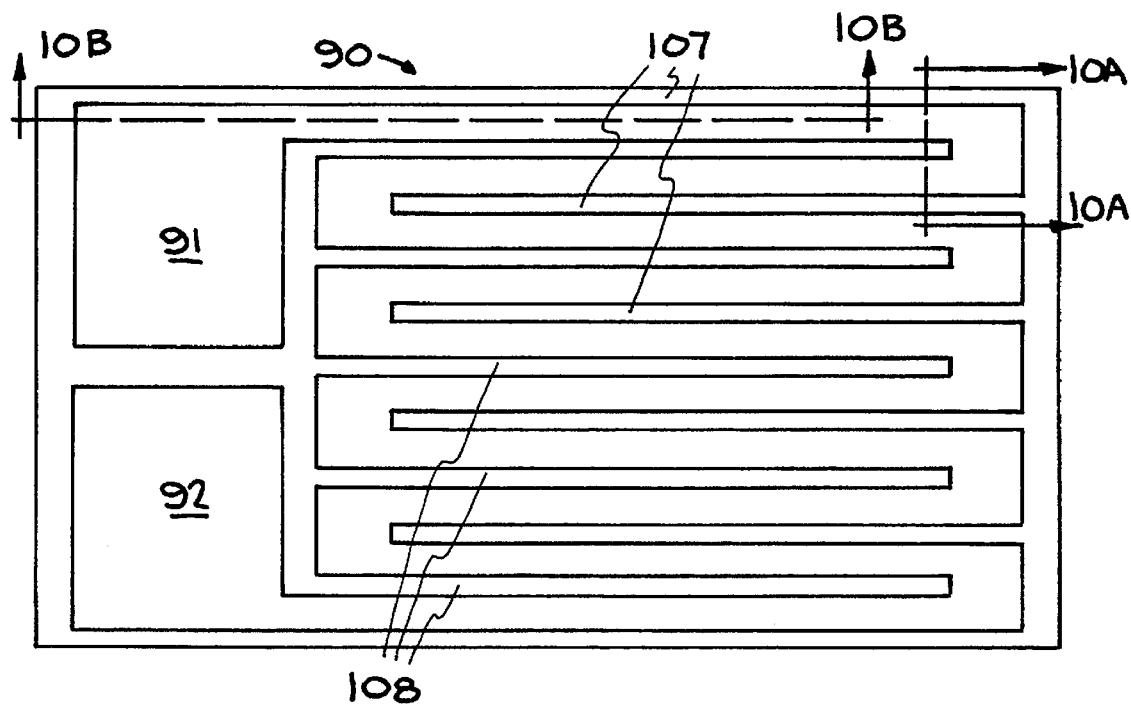
Figure 11:
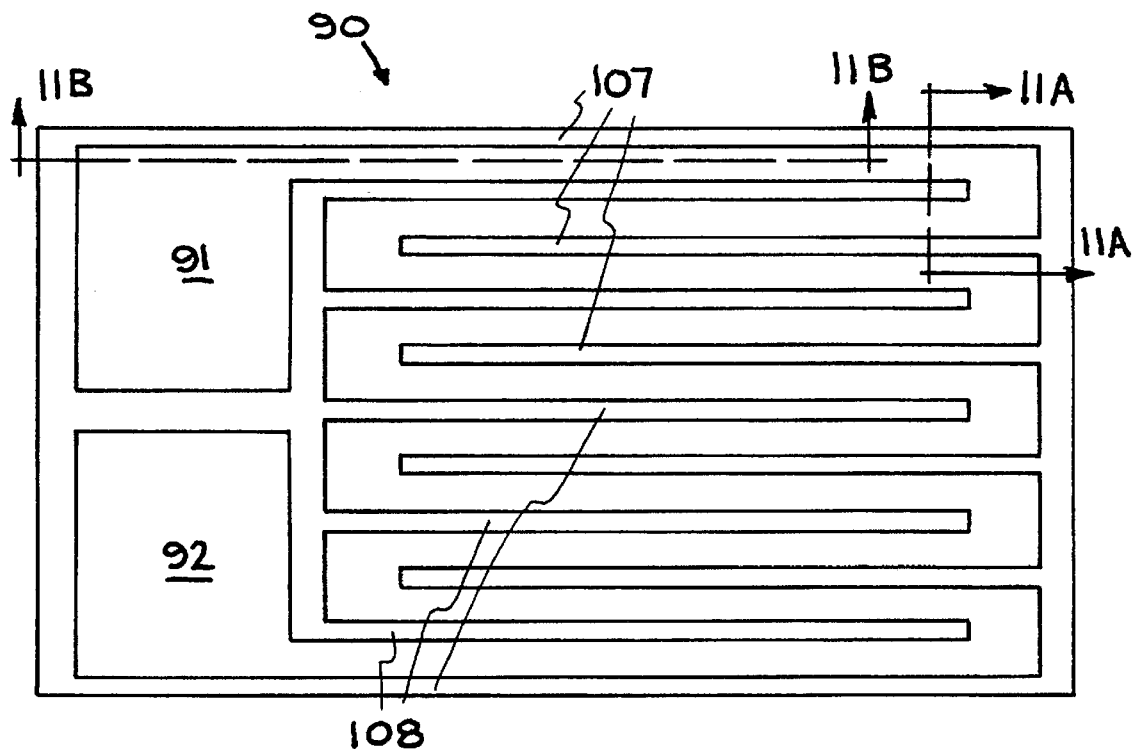
FIGS. 11, 11A and 11B illustrate another embodiment of the heater of FIG. 9A, with the cross-sections of FIGS. 11A and 11B greatly enlarged.

The heating of the microgripper of FIG. 7 was applied by an integrated circuit (IC) fabricated thin film resistor heater pad, as described in greater detail with respect to FIGS. 10 and 11. The heater pad is placed on the microgripper cantilevers and current is applied, the heat is transferred from the heater to the Si gripper cantilevers for phase transformation in the Ni—Ti—Cu film to take place. Thus, remote active heating of the SMA film can be accomplished.

Also, the microgripper of FIG. 7 is being integrated with strain sensor for feedback control as described hereinafter with respect to FIG. 12.

Figures 9A, 9B:
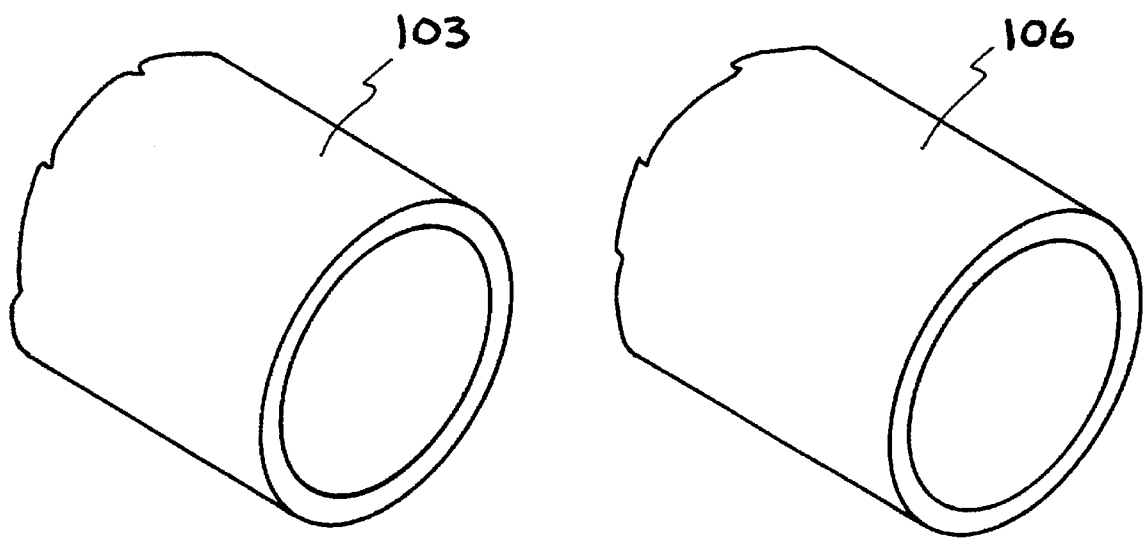
FIGS. 9, 9A and B illustrate resistive heaters and electrical feedthrough for FIG. 7 a microgripper.
Figure 9:
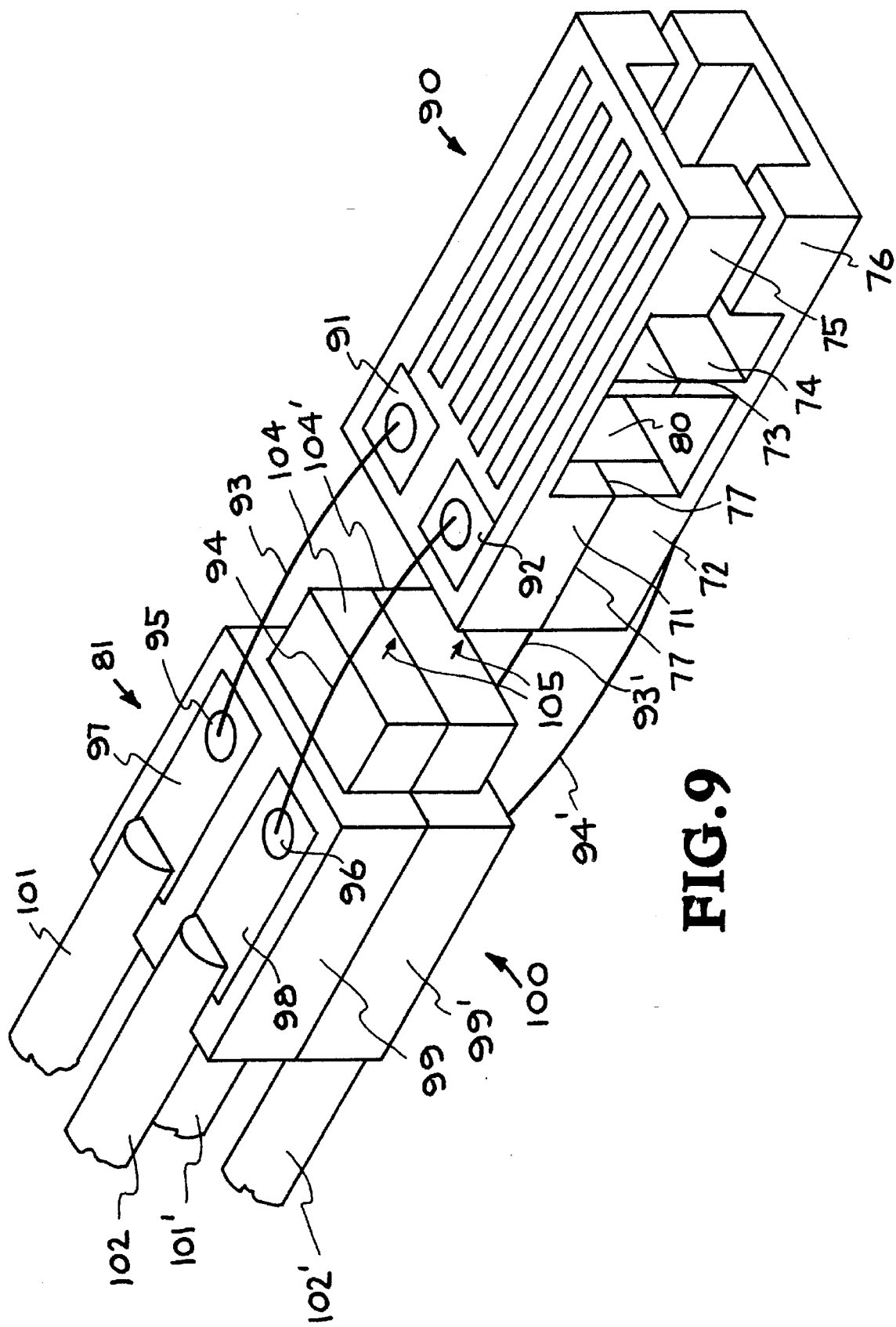

FIGS. 9, 9A and 9B illustrate packaging of the microgripper of FIG. 7 on a catheter. Components similar to those of FIG. 7 are given corresponding reference numerals. The microgripper 70 is electrically connected to a wiring jacket 81' via a SMA film resistive heater, generally indicated at 90 on cantilever 71 and having contract pads 91 and 92, which are connected via leads 93 and 94 to contact pads 95 and 96 on conductive films 97 and 98 such as copper, bonded to a polymide member 99, of an electrical feedthrough ribbon generally indicated at 100. As indicated by leads 93' and 94', an identical resistive heater and electrical connection arrangement is provided between cantilever 72 of microgripper 70 and the conductive film on polymide member 99' of wiring jacket 81. The polymide members 99 and 99' and associated copper films are connected to insulated feedthrough wires 101/102 and 101'/102' of ribbon 100, and are located within a catheter tube 103 (see FIG. 9A). The polymide members 99 and 99' include protruding end sections 104 and 104' which, as indicated by the arrows 105, extend into the hollow channel 80 of microgripper 70. The wiring jacket 81' is secured to microgripper 70 by a heat shrink tube 106 (see FIG. 9B).

Figure 10A:
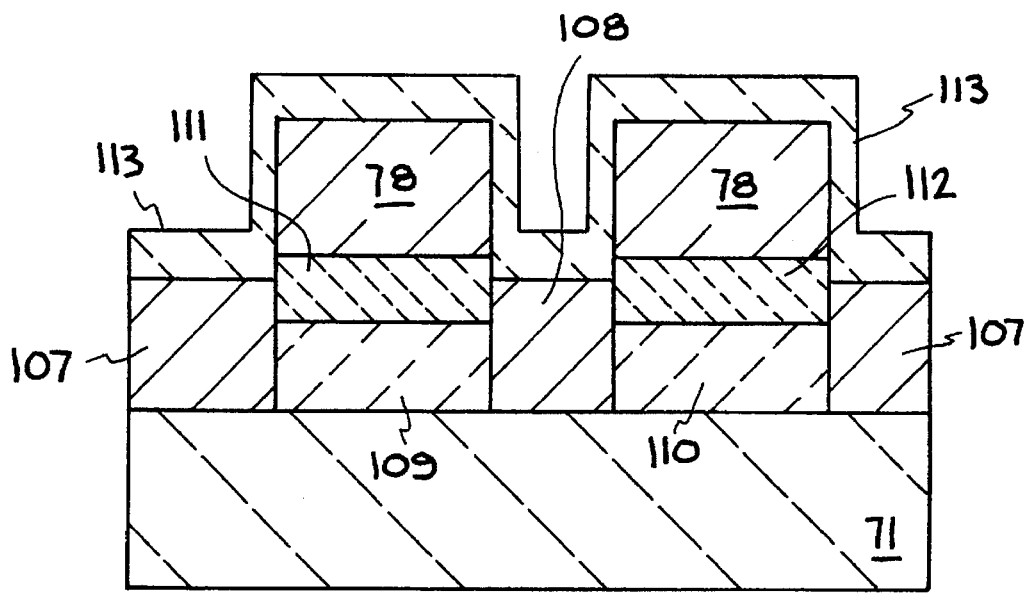
Figure 10:
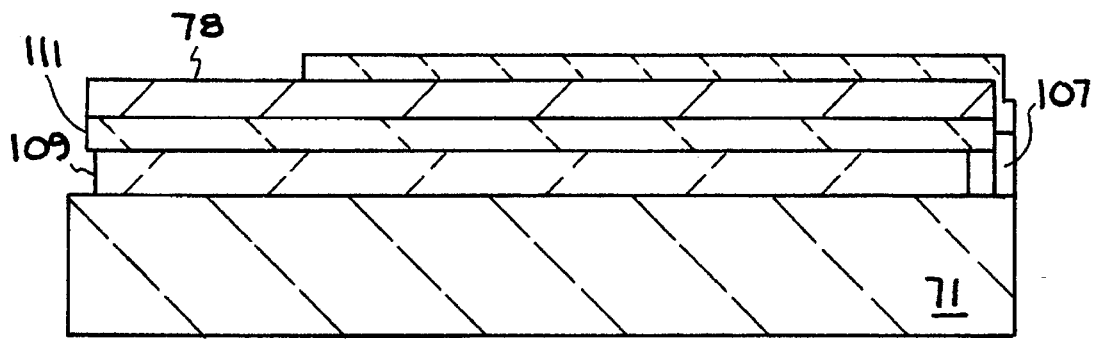
Figure 11A:
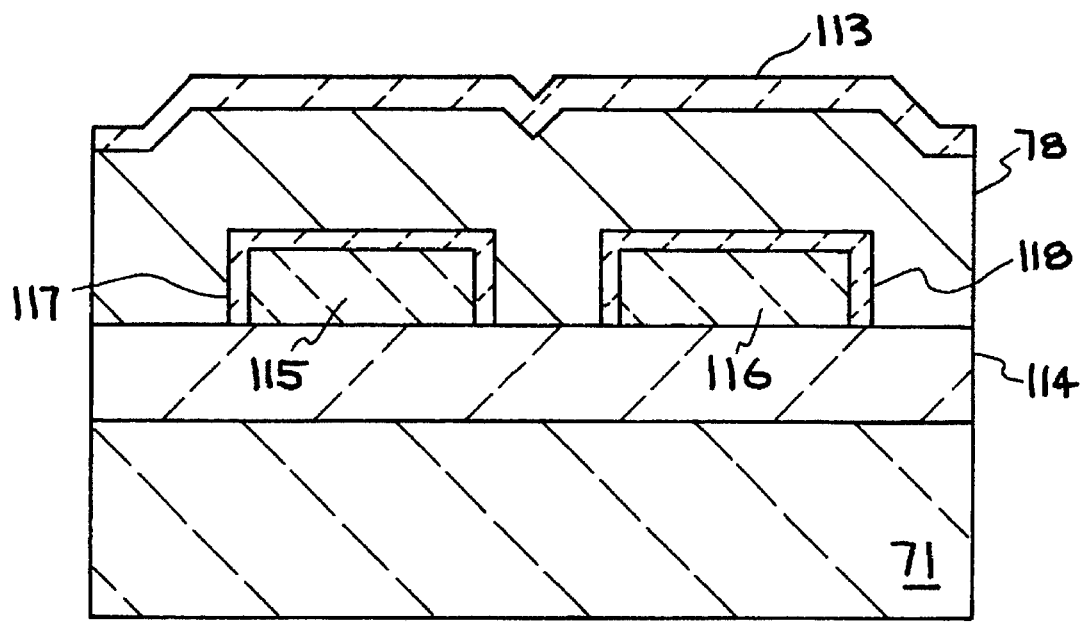
Figure 11B:
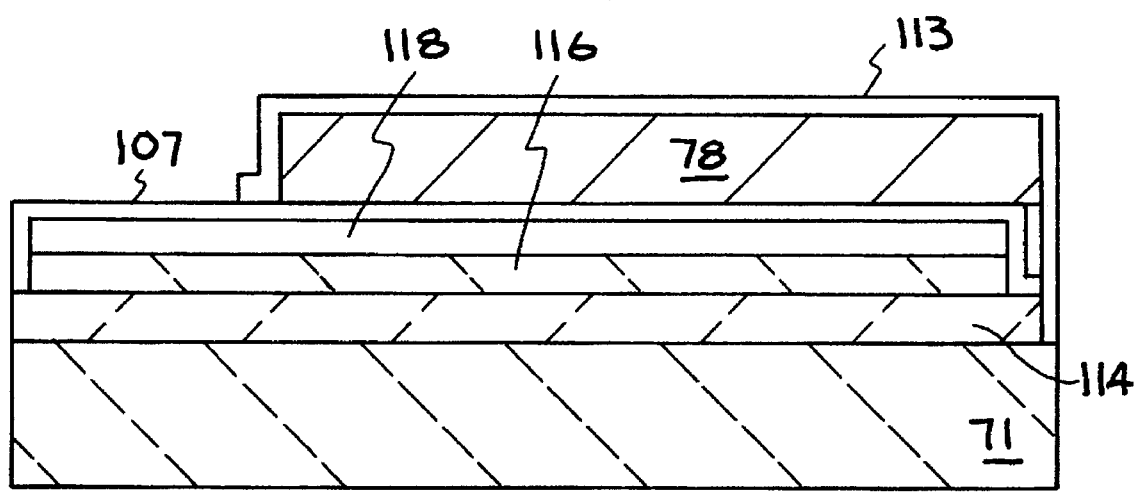

The resistive heaters 90° of FIG. 9 located on cantilevers 71 and 72 of the microgripper 70 may be of the type illustrated in FIGS. 10, 10A and 10B or of the type illustrated in FIGS. 11, 11A and 11B, each having piezoresistive feedback capabilities.

In the FIG. 10 embodiment, the resistive heater 90 includes contact pads 91 and 92, as in FIG. 9, with resistive wires 107 being in electrical contact with pad 91 and resistive wires 108 being in contact with pad 92. FIG. 10A is a greatly enlarged section of FIG. 10 and composed of a silicon beam (cantilever 71), SMA resistive wires 107, 108, 107, of resistive heater 90, between which are layers 109 and 110 of an oxide, on top of which are layers 111 and 112 of polysilicon (poly-Si), and on top of which are sections of the SMA thin film 78, covered by an oxide or protective layer 113. FIG. 10B is an enlarged cross-sectional side view of the FIG. 10 embodiment.

The resistive heater 90 of FIGS. 11, 11A and 11B is generally similar to the FIG. 10 embodiment, and similar reference numbers will be utilized. In FIG. 11, the resistive heater 90 includes contact pads 91 and 92, with resistive wires 107 connected to pad 91 and resistive wires 108 connected to pad 92, as in the FIG. 10 embodiment. FIG. 11A is a greatly enlarged view of a section of FIG. 11 and composed of a silicon beam (cantilever) 71, an oxide layer 114, a pair of polysilicone (poly-Si) layers 115 and 116 on which is deposited oxide (LTO) layers 117 and 118, the SMA thin film 78 and an oxide or protective layer 113. FIG. 11B is an enlarged cross-sectional side view of the FIG. 11 embodiment.

Figure 12:
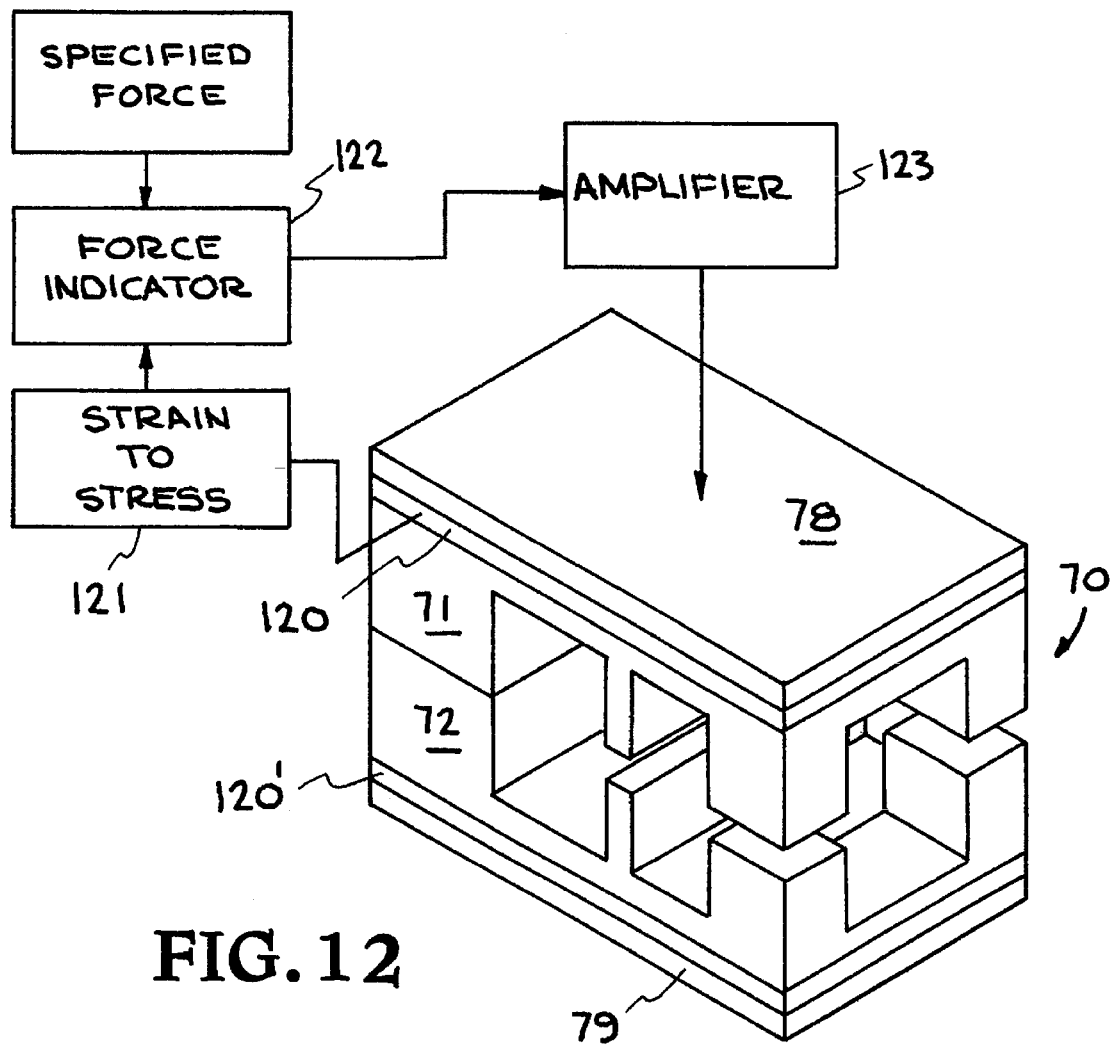
FIG. 12 illustrates a force feedback control system for the microgripper of FIG. 7.

FIG. 12 schematically illustrates a force feedback control of the microgripper 70 of the FIG. 7 embodiment, and similar components are given corresponding reference numerals. A sensing film 120 is deposited on a cantilever 71 and is connected via a strain-to-stress conversion, indicated at 121, as discussed above, to a specified force indicator 122, the output of which is directed through signal processor (amplifier) 123 to an actuation film (SMA film 78). While not shown, the lower cantilever 72 is provided with a similar arrangement.

Figure 13:
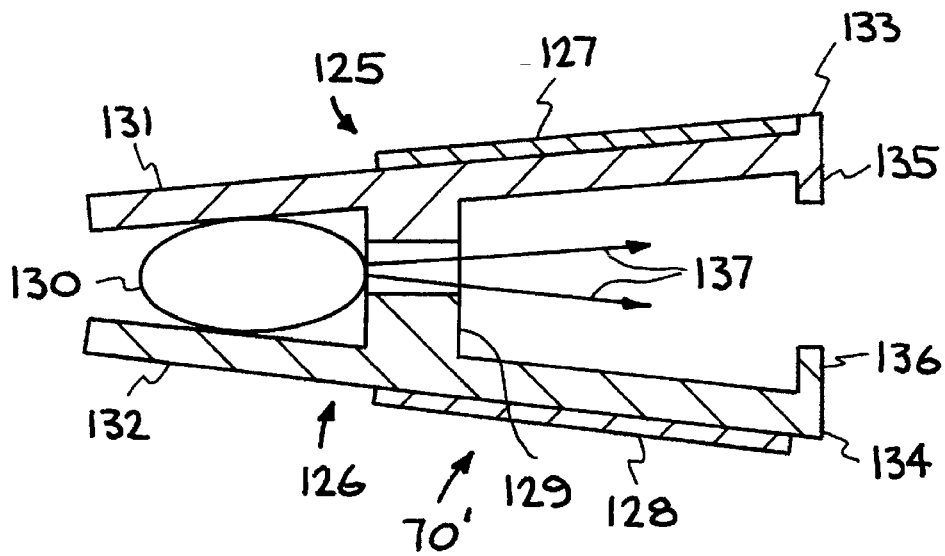
FIG. 13 is a view of an SMA film activated microactuator made in accordance with the invention for providing hydraulic pressure/fluid delivery from a microballoon.

The FIG. 7 embodiment can be modified to provide a hydraulic pressure/fluid delivery system, as illustrated in FIG. 13. Here, cantilevers 125 and 126 of a microactuator 70' are provided with SMA thin films 127 and 128, respectively, with cantilevers 125 and 126 being connected by a section 129 having an opening, not shown, therein. A microballoon 130 is position intermediate one end 131 and 132 of cantilevers 125 and 126, while the other end 133 and 134 thereof is provided with grippers or jaws 135 and 136. Upon actuation, ends 131/132 of the cantilever move inwardly, as indicated by the arrows, while the ends 133 and 134 move outwardly, as indicated by the arrows, whereby fluid within the microballoon 130 is forced therefrom as indicated by the arrows 137, thereby delivering the fluid 137 to a point of use.

It has thus been shown that the present invention provides an electromechanical micromechanism (either IC silicon-based or precision micromechanical) which will, for example, extend and improve the application of catheter-based interventional therapies for the repair of arterio-aneurysms in the brain or other interventional clinical therapies. The microgripper of this invention, in addition to medical applications, has non-medical uses, such as micro assembling and for remote and precise manipulation of small objects, and has the capability to operate in small areas having 250 μm diameters, such as small blood vessels.

While particular embodiments, materials, parameters, etc., having been set forth to exemplify the invention, such are not intended to be limiting. Modifications and changes may become apparent to those skilled in the art, and it is intended that the invention be limited only by the scope of the appended claims.

We claim:

1. A microgripper, comprising:
   a pair of flexible members constructed to have a cross-section capable of operating in an area having a diameter as small as 250 μm,
   at least one of said flexible members being adapted to grip an associated object, and
   means in contact with said member for retaining said member in gripping contact with an associated object, and for releasing said member from gripping contact with an associated object.

2. The microgripper of claim 1, wherein said pair of flexible members comprises a pair of coils, one of said pair of coils being adapted to grip an associated object, another of said pair of coils being adapted to force an associated object from said one of said pair of coils.

3. The microgripper of claim 2, wherein one coil of said pair of coils is larger in diameter than another coil of said pair of coils.

4. The microgripper of claim 1, wherein said flexible members comprises a pair of flexible gripping arms, said gripping arms having flexible gripper members at one end and are secured together at an opposite end.

5. The microgripper of claim 4, wherein said means includes an expandable device.

6. The microgripper of claim 4, wherein said means includes shaped-memory alloy films.

7. The microgripper of claim 4, wherein said means includes a compressive thin film.

8. The microgripper of claim 7, wherein said means additionally includes a shape-memory alloy wire.

9. The microgripper of claim 4, wherein each of said gripping arms is provided with means which allows an outer portion thereof to flex with respect to each other.

10. The microgripper of claim 4, wherein said gripping arms define a hollow channel therebetween.

11. The microgripper of claim 4, wherein each of said gripping arms include a pusher pad located in spaced relation to said gripper members.

12. The microgripper of claim 4, wherein said pair of gripping arms are constructed of silicon.

13. The microgripper of claim 1, additionally including means containing a fluid located between said pair of flexible members, whereby movement of said pair of members forces fluid from said means.

14. The microgripper of claim 1, additionally including heating means for causing movement of said pair of flexible members.

15. The microgripper of claim 14, additionally including shape-memory film on each of said pair of members, said heating means causing movement of said shape-memory film thereby causing movement of said pair of members.

16. The microgripper of claim 1, wherein said pair of flexible members are bonded together by Au—Si eutectic bonding.

17. The microgripper of claim 16, wherein the eutectic bonding of said pair of members is carried out by depositing an adhesive layer on at least one of the Si members, depositing an Au layer of the adhesive layer, annealing to the eutectic point of the Au layer, and pressurizing the Si members together for a time period, whereby a highly uniform and solid bond is formed.

18. A micromechanism adapted to be attached to a forward end of a catheter for use as a biopsy sampler or for use in interventional therapies, comprising:

a pair of bendable members connected at one end thereof and adapted to move at the other end thereof, said pair of bendable members being constructed to have a cross-section capable of operating in an area having a diameter as small as about 250 μm, each of said pair of bendable members including at least one gripper located at said other end thereof, and means in contact with at least one of said pair of bendable members for causing movement of said other end thereof.

19. The micromechanism of claim 18, wherein each of said pair of bendable members additionally includes a pusher pad located in spaced relationship to said gripper.

20. The micromechanism of claim 18, wherein each of said pair of bendable members include a cantilever section.

21. The micromechanism of claim 20, wherein said means for causing movement of said other end of said pair of members comprises an expandable device.

22. The micromechanism of claim 18, wherein said means for causing movement of said other end of said pair of bendable members includes a quantity of a shape-memory alloy.

23. The micromechanism of claim 22, wherein said quantity of a shape-memory alloy is in the form of a wire, and wherein said pair of members include means into which said wire is removably inserted.

24. The micromechanism of claim 22, wherein said quantity of a shape-memory alloy is in the form of a film.

25. The micromechanism of claim 24, wherein said film extends along a surface of each of said pair of members.

26. The micromechanism of claim 25, wherein said film is located on an outer surface of each of said pair of members.

27. The micromechanism of claim 26, wherein said pair of members are constructed to form a hollow channel through said connected ends.

28. The micromechanism of claim 25, wherein said film is located on an inner surface of each of said pair of members.

29. The micromechanism of claim 28, wherein each of said pair of members includes a reduced cross-section portion located adjacent said film.

30. The micromechanism of claim 23, wherein each of said pair of members include a section containing a compressive film.

* * * * *